United States Patent [19]

Drauz et al.

[11] Patent Number: 5,585,500

[45] Date of Patent: Dec. 17, 1996

[54] METHOD OF PRODUCING OPTICALLY ACTIVE PYRROLIDINES WITH HIGH ENANTIOMERIC PURITY

[75] Inventors: Karlheinz Drauz; Matthias Kottenhahn, both of Freigericht; Michael Kraft, Rodenbach; Michael Schwarm, Alzenau, all of Germany

[73] Assignee: Degussa Aktiengesellschaft, Frankfurt am Main, Germany

[21] Appl. No.: 501,282

[22] Filed: Jul. 17, 1995

[30] Foreign Application Priority Data

Jul. 15, 1994 [DE] Germany .................. 44 25 071.1

[51] Int. Cl.⁶ .............................. C07D 207/12
[52] U.S. Cl. ........................... 548/541; 548/545
[58] Field of Search .......................... 548/541

[56] References Cited

FOREIGN PATENT DOCUMENTS 0185882 10/1985 European Pat. Off. .

OTHER PUBLICATIONS

A. Abiko et al., "An Improved, Convenient Procedure for Reduction of Amino Acids to Aminoalcohols:" Use of $NaBH_4$ 14 $H_2SO_4$, Tetrahedron Letters, vol. 33, No. 38, 1992, pp. 5517–5518.

Primary Examiner—David B. Springer
Attorney, Agent, or Firm—Cushman Darby & Cushman IP Group of Pillsbury Madison & Sutro LLP

[57] ABSTRACT

A method of producing optically active pyrrolidines of the general formula

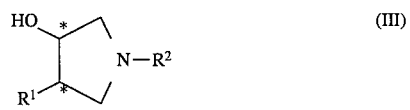

in which
$R^1$ is hydrogen or OH,
$R^2$ is a benzyl group which can have one or more alkyl-, alkoxy- and/or halogen substituents on the aromatic, and
\* is and/or can be an asymmetric center,
by reducing the corresponding, enantiomerically pure pyrrolidinediones using activated alkali boron hydride.

9 Claims, No Drawings

METHOD OF PRODUCING OPTICALLY ACTIVE PYRROLIDINES WITH HIGH ENANTIOMERIC PURITY

BACKGROUND OF THE INVENTION

1. Field of the Invention

The invention describes a novel method for producing [preparing] optically active 3-hydroxy- or 3,4-dihydroxy-pyrrolidines. The invention is relative in particular to a method of producing optically active pyrrolidines with high enantiomeric purity with the general formula

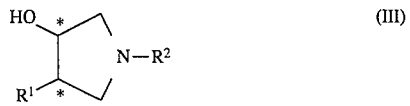

in which $R^1$ can be hydrogen or a hydroxy group, $R^2$ is a benzyl group whose aromatic group can have one or more alkyl, alkoxy and/or halogen substituents and * is an asymmetric center, when the carbon atom so characterized carries a hydroxy group, by means of the reduction of enantiomerically pure 2,5 pyrrolidinediones of the general formula

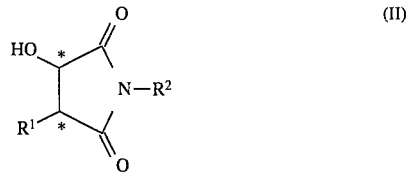

in which $R^1$, $R^2$ and * have the meanings indicated for formula (III).

2. Description of Related Art

These compounds are important intermediates in the chemical industry. Thus, enantiomers of 3-hydroxypyrrolidine, which are obtained from compounds of formula III ($R^1$=H) by catalytic hydrogenation, are structural elements in the synthesis of carbapenem antibiotics (Chemotherapy 1991, 39 (suppl. 3), 83 ff.; Tetrahedron Lett. 1984, 25 (26), 2793; JP 04036282 A2, Feb. 6, 1992; JP 03275685 A2, 12-6-91; Korean J. Med. Chem. 1993, 3 (1), 72). Enantiomers of 1-benzyl-3,4-dihydroxypyrrolidine are used in the synthesis of optically active phosphanes which serve as ligands of metallic catalysts for asymmetric hydrogenations (Chem. Ber. 1986, 119, 3326; DE 34 46 303 A1, Jun. 19, 1986; DE 34 03 194 A1, Aug. 1, 1985; Bull. Chem Soc. Jpn. 1984, 57 (3), 823).

Various methods have been described for the production of these compounds. Thus, optically active 3-hydroxypyrrolidines have been obtained by means of classic (JP 05279326 A2, Oct. 26, 1993; JP 05279325 A2, Oct.26, 1993; JP 05032620, Feb. 9, 1993; JP 04164066 A2, Jun. 9, 1992; JP 04013659 A2, Jan. 17, 1992; JP 61063652 A2, Apr. 1, 1986) or enzymatic racemate splitting (JP 05227991 A2, Sep. 7, 1993; JP 04131093 A2, May 1, 1992; JP 01141600 A2, Jun. 2, 1989). A disadvantage of these methods is the fact that the maximum yield is only 50% if the undesired enantiomer can not be returned [restored] by a racemization.

Another possibility is the decarboxylation of optically active hydroxyproline (JP 05255204 A2, Oct. 5, 1993; Bioorg. Med. Chem. Lett. 1992, 2 (8), 827; Chem. Lett. 1986 (6) 893; JP 60023328 A2, Feb. 5, 1985). This is problematic in as far as the suitable, optically active hydroxyproline is an expensive initial material which is often not available in large amounts.

Further methods are based on the cyclization of suitable butane or butyric-acid derivatives which must then, if necessary, be further converted chemically (EP 452143 A2, Oct. 16, 1991; EP 431521 A1, Jun. 12, 1991; EP 347818 A2, Dec. 27, 1989; JP 01045360 A2, Feb. 17, 1989; EP 269258 A2, Jun. 1, 1988). Syntheses starting from L-glutamic acid (Synth. Comm. 1986, 16 (14), 1815) and N-substituted 3-pyrrolines (J. Org. Chem. 1986, 51 (22), 4296) are also known. These methods require a comparatively expensive chemistry or start from precursors which are not readily obtainable.

Optically active malic and tartaric acids are very well-suited educts which are readily and inexpensively available in large amounts. They can be cyclized with benzyl amine relatively easily to the corresponding imides, which can then be reduced to the optically active hydroxy pyrrolidines and optionally be debenzylated hydrogenolytically. However, a danger thereby is the described cyclization of tartaric acid with benzyl amine in xylene since the imide formed thereby crystallizes out toward the end of the reaction "under vigorous boiling up" (Chem. Ber. 1986, 119, 3327). The reduction of the imides to the hydroxypyrrolidines is easy in principle but in the past it could only be carried out with comparatively expensive reagents which are at times problematic as concerns the safety engineering or for reasons of environmental protection, e.g. sodium boron hydride boron trifluoride etherate (Chem. Ber. 1986, 119, 3327), sodium aluminum hydride (JP 03200762 A2, Sep. 2, 1991), $Na[AlH_2(OCH_2CH_2OMe)_2]$ (JP 01254657 A2, Oct. 11, 1989) or lithium aluminum hydride (JP 01207266 A2, Aug. 21, 1989).

Considering the state of the art presented herein, the invention has the problem of making available a further method for the production of compounds of the initially cited type which permits the obtention of the desired, optically active pyrrolidines in high enantiomeric purity using readily and inexpensively obtainable educts and which at the same time can be carried out with the least expense possible.

These and other problems which are not cited in detail are solved by means of a method of the initially mentioned type with the features of the characterizing part of claim 1.

SUMMARY OF THE INVENTION

The fact that an activated alkali boron hydride is used for the reduction of the compound of formula II makes available a reduction variant which is simple to carry out, can be well-handled especially even on an industrial scale and, in addition, brings about a surprisingly high enantiomeric purity of the products.

The reduction of the imides of formula II to the corresponding, optically active 1-substituted-3-hydroxy- or 3,4-dihydroxypyrrolidines (compounds of formula III) proceeds within the framework of the invention according to the following formula scheme:

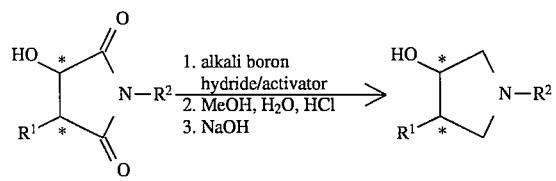

According to the invention the alkali boron hydride to be used for the reduction is always to be activated. Activators which are preferably to be used to this end are, among others, iodine, hydrogen chloride and/or sulfuric acid. Of the activators named, sulfuric acid is quite especially preferred for the invention.

The alkali boron hydrides to be used with advantage in the invention include lithium-, sodium- and potassium boron hydride. Of them, lithium- and sodium boron hydride are preferred and sodium boron hydride is especially preferred on account of its low price.

The reduction systems cited are simple and, especially on an industrial scale, comparatively safe to handle. The residues of these reagents remaining after the reaction can be disposed of relatively easily in comparison to the systems used in the past (see above). The group $R^2$ is a benzyl group, as already mentioned, whose aromatic component can carry one or more alkyl-, alkoxy- and/or halogen substituents. Preferred alkyl groups are $C_1$–$C_4$, also branched; preferred alkoxy substituents are methoxy, ethoxy, propoxy and isopropoxy; preferred halogens are F, Cl, Br, I.

In a preferred embodiment of the invention the group $R^2$ is a benzyl group and the alkali boron hydride used is $NaBH_4$. The method of the invention proceeds in this instance in conformity with the following equation:

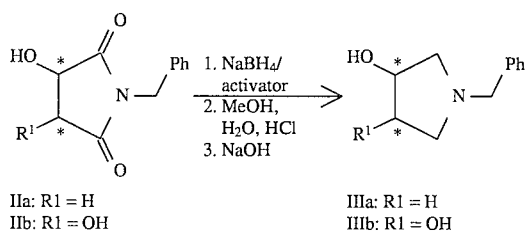

IIa: R1 = H
IIb: R1 = OH

IIIa: R1 = H
IIIb: R1 = OH

The system sodium boron hydride/iodine is already known for the reduction of a plurality of classes of compounds such as amino acids (Tetrahedron Lett. 1992, 33, 38, 5517), amino acids, N-acyl amino acids and amino-acid amides (J. Org. Chem. 1993, 58, 3568), carboxylic acids (J. Org. Chem. 1991, 56, 5964), esters, amides and nitriles (Tetrahedron 1992, 48 (22), 4623). On the other hand, the systems sodium boron hydride/sulfuric acid and sodium boron hydride/hydrogen chloride have previously been described only for the reduction of amino acids and N-acyl amino acids to the corresponding amino- and N-alkyl amino alcohols (Tetrahedron Lett. 1992, 33 (38), 5517). It was now found that these reduction systems can be used in accordance with the invention in an especially advantageous manner for the reduction of the imides IIa and IIb to the pyrrolidines IIIa and IIIb; it turned out thereby in a surprising and advantageous manner that the stereochemistry on the chirality centers carrying the hydroxy group remained completely preserved. In addition, the reactions proceed in a clean fashion and with good crude yield.

It is basically advantageous for the method of the invention if it is carried out in a solvent.

The solvent used for the reduction should have a sufficient dissolving power for the reaction partners used. 1,2-Dimethoxyethane and tetrahydrofurane are especially preferable; however, in principle even other ethers as well as alcohols and acetals can be considered.

The reaction can be carried out within a broad temperature range (approximately −20° C.—boiling temperature of the solvent); however, it is preferable to proceed in such a manner that the imide (e.g. the compound IIa or IIb) is placed with alkali boron hydride in the solvent, a solution of the activator (preferably iodine or sulfuric acid) is added dropwise into the latter or another suitable solvent at 0°–40° C. under optional cooling and subsequently heated several hours up to a maximum of the boiling temperature of the solvent used until the reaction is completed. 2–5 moles, preferably 3–4 moles reducing agent (preferably sodium boron hydride) are used per mole imide of compound II. It is advantageous to add 1 equivalent hydrogen chloride or ½ equivalent iodine (as $I_2$) or sulfuric acid as activator per mole alkali boron hydride.

After the reaction has ended the reaction mixture is hydrolyzed with an alcohol and/or water, the organic solvent distilled off, the residue taken up in the water and made acidic with hydrochloric acid or another acid, agitated for a while, then made alkaline, preferably with sodium hydroxide solution, and the pyrrolidine of formula III extracted with a suitable organic solvent. It can then be isolated as oil or in crystalline form or as hydrochloride and be further purified, as required, by chromatography or recrystallization.

The optically active 2,5-pyrrolidinediones (formula II) to be used for the reduction are obtained in an advantageous further development of the method of the invention by means of the condensation of optically active compounds of formula I with a compound of formula IV. The following formula scheme serves for clarification:

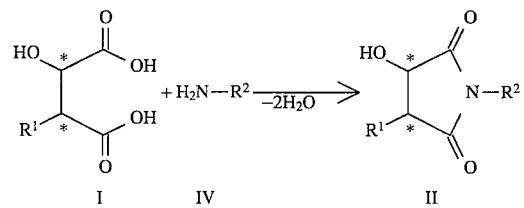

I            IV            II

In these formulas $R^1$ signifies hydrogen or a hydroxy group, $R^2$ a benzyl group whose aromatic group can comprise alkyl-, alkoxy- and/or halogen substituents and * an asymmetric center if the carbon atom so characterized carries a hydroxy group.

Benzyl amine as compound IV is quite especially preferred for the invention.

It is therefore furthermore especially advantageous if an optically active malic acid (Ia) or tartaric acid (Ib) is cyclized with benzyl amine to the optically active 1-benzyl-3-hydroxy- (IIa) or 1-benzyl-3,4-dihydroxy-2,5-pyrrolidinedione (IIb). It was surprisingly and advantageously found thereby that the reaction in boiling cumene instead of in xylene can be carried out not only without danger and in a readily controllable manner but it also proceeds practically quantitatively with the end of the separation of water and the imide formed can be further processed after the solvent has been distilled off without further purification as crude product, which has a favorable effect on the total yield.

This reaction is presented once again in the following scheme:

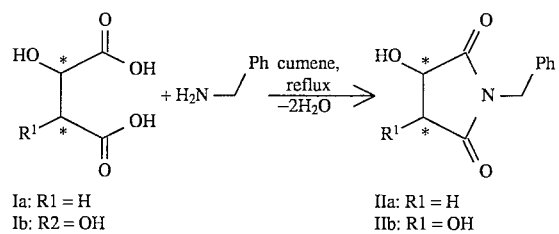

Ia: R1 = H
Ib: R2 = OH

IIa: R1 = H
IIb: R1 = OH

In all, a simple and economic access to optically active 1-benzyl-3-hydroxy- or 1-benzyl-3,4-dihydroxypyrrolidine is described with this novel method. It is explained in detail in the following exemplary embodiments:

DESCRIPTION OF THE PREFERRED EMBODIMENTS

Example 1

A mixture of 50.0 g (0.373 mole) (S)-malic acid (Ia), 41 ml (0.373 mole) benzyl amine and 250 ml cumene was heated with an internal temperature of 155° C. for 2.5 h on a water separator, during which time 12 ml water were separated. An oily phase formed during cooling off which slowly crystallized. The cumene was decanted off thereafter and the residue crystallized out of 220 ml EtOH. 30.3 g (39.6%) (S)-1-benzyl-3-hydroxy-2,5-pyrrolidinedione (IIa) were isolated in the form of colorless crystals.

Melting point: 110°–113° C.

$[\alpha]D20$: −57.3° (1.0, EtOH)

C11H11NO3 calc.: C 64.38 H 5.40 N 6.83 205.21 obs.: C 64.03 H 5.44 N 6.96

A further 8.7 g (11.4%) IIa were obtained from the mother liquor by evaporation to low bulk.

Example 2

A solution of 63.4 g (0.25 mole) iodine in 200 ml DME was added dropwise to a suspension of 25.6 g (0.125 mole) (S)-1-benzyl-3-hydroxy-2,5-pyrrolidinedione (IIa) and 19 g (0.5 mole) sodium boron hydride in 150 ml DME within 3 h at 25°–33° C. The mixture was subsequently agitated overnight at 70° C. After cooling off, 40 ml MeOH were added and the batch was evaporated to dryness. The residue was taken up in 120 ml water and agitated with 30 ml conc. hydrochloric acid and 150 ml toluene overnight at room temperature. After alkalization with 45 ml 50% sodium hydroxide solution the toluene phase was separated off at 70° C. and the aqueous phase subsequently extracted [re-extracted] with 100 ml toluene. The toluene phases were evaporated to dryness after drying over sodium sulfate, during which 20.3 g (91.6%) (S)-1-benzyl-3-hydroxypyrrolidine (IIIa) were obtained as oil.

$[\alpha]D20$: −3.6° (1,5, MeOH)

Example 3

A solution of 13.4 ml (0.25 mole) sulfuric acid in 40 ml DME was added dropwise to a suspension of 25.6 g (0.125 mole) (S)-1-benzyl-3-hydroxy-2,5-pyrrolidine dione (IIa) and 19 g (0.5 mole) sodium boron hydride in 150 ml DME within 1.5 h at 35° C. The mixture was subsequently agitated 2 h at 70° C. After cooling off, 40 ml MeOH were added and the batch was evaporated to dryness. The residue was taken up in 120 ml water and agitated overnight at room temperature with 30 ml conc. hydrochloric acid and 150 ml toluene. After alkalization with 45 ml 50% sodium hydroxide solution the toluene phase was separated off at 70° C. and the aqueous phase subsequently extracted [re-extracted] with 100 ml toluene. The toluene phases were evaporated to dryness after drying over sodium sulfate, during which 22.7 g oil were obtained. It was taken up in 150 ml toluene, 100 ml water and 15 ml conc. hydrochloric acid and agitated overnight at room temperature. After repetition of the described workup 21.7 g (97.9%) (S)-1-benzyl-3-hydroxy-pyrrolidine (IIIa) were obtained as oil.

$[\alpha]D20$: −3.6° (1.5, MeOH).

Example 4

A mixture of 100 g (0.745 mole) (S)-malic acid (Ia), 81.4 ml (0.745 mole) benzylamine and 500 ml cumene was boiled under nitrogen at 153° C. oil-bath temperature for 2.5 h on a water separator, during which 25 ml water were separated. The mixture was subsequently rotated [spun] in to dryness, taken up in 250 ml DME and rotated in again to dryness.

158 g (approximately 0.745 mole) crude (S)-1-benzyl-3-hydroxy-2,5-pyrrolidinedione (IIa) were obtained. It was dissolved in 800 ml DME to which 85.1 g (2.25 moles) sodium boron hydride were then added. A solution of 60.3 ml (1.125 moles) sulfuric acid in 200 ml DME was added dropwise to the thick suspension produced at 20°–32° C. within 2.5 h and subsequently agitated 3 h at 70° C. After cooling off, 200 ml methanol were added dropwise and the batch was subsequently rotated in to dryness. The residue was taken up in 700 ml water, compounded under ice cooling with 180 ml conc. hydrochloric acid and agitated 1 h until the end of the development of gas. Then, 270 ml sodium hydroxide solution and 1 l toluene were added. After the mixture was heated to 70° C. the toluene phase was separated and the aqueous phase subsequently extracted with 300 ml toluene. After the rotating in of the organic phase the residue began to gas, so that it was taken up in 600 ml water and 600 ml toluene and agitated overnight at room temperature with 90 ml conc. hydrochloric acid. The mixture was then made basic again and extracted and rotated in as above, yielding 131.3 g (99.4%) crude (S)-1-benzyl-3-hydroxypyrrolidine (IIIa).

The structure of IIIa was corroborated by an NMR spectrum.

Example 5

A solution of 50.7 g (0.2 mole) iodine in 200 ml THF was added dropwise to a suspension of 22.1 g (0.1 mole) (3R,4R)-1-benzyl-3,4-dihydroxy-2,5-pyrrolidinedione (IIb) and 15.2 g (0.4 mole) sodium boron hydride in 500 ml THF within 1 h at 12°–15° C. The mixture was then heated 2 d under argon on a reflux. After cooling off, 50 ml methanol were added and after the end of the development of gas the mixture was evaporated to dryness. The residue was taken up in 60 ml water and compounded with 15 ml conc. hydrochloric acid until an acidic reaction. After 30 min agitation, 150 ml 20% potash lye were added and [the mixture] extracted twice with 250 ml MTBE each time. After evaporation, 19.2 g colorless, crystalline residue remained. Recrystallization from 60 ml ethyl acetate yielded in 2 fractions 10.4 g (53.9%) (3S,4S)-1-benzyl-3,4-dihydroxypyrrolidine (IIIb).

Melting point: 99°–100.5° C.

$[\alpha]D20$: +32.7° (1.5, MeOH)

C11H15NO2 calc.: C 68.37 H 7.82 N 7.25 193.25 obs.: C 68.10 H 7.89 N 7.42

Example 6

A solution of 32.2 ml (0.6 mole) sulfuric acid in 100 ml DME was added dropwise to a suspension of 66.4 g (0.3 mole) (3R,4R)-1-benzyl-3,4-dihydroxy-2,5-pyrrolidine dione (IIb) and 45.6 g (1.2 moles) sodium boron hydride in 400 ml 1,2-dimethoxyethane (DME) within 2.5 h at room temperature. The mixture was then agitated 4 h at 75° C. After it cooled off, 75 ml MeOH were added and the mixture rotated in to dryness. The residue was taken up in 300 ml water and compounded with 50 ml conc. hydrochloric acid. The mixture was then made alkaline and extracted with 200 ml toluene twice at 65° C. The extraction residue was taken up in 100 ml each of water and toluene, adjusted to be strongly acidic with hydrochloric acid and agitated overnight at room temperature. It was then made alkaline with 30% sodium hydroxide solution. After the addition of 200 ml toluene the organic phase was separated at 65° C. The aqueous phase was extracted again with 200 ml methylene chloride. After the organic phases were rotated in, 85 g oil remained. The latter was taken up in 400 ml ethyl acetate and washed twice with 80 ml water at 65° C. The ethylacetate phase was rotated in after drying over sodium sulfate. 60 g residue remained which was recrystallized from 150 ml ethyl acetate. 30.2 g (52.1%) (3S,4S)-1-benzyl-3,4-dihydroxypyrrolidine (IIIb) were obtained in two fractions.

Melting point: 97°–98° C.

$[\alpha]D20$: +33.5° (1.5, MeOH)

C11H15NO2 calc.: C 68.37 H 7.82 N 7.25 193.25 obs.: C 68.30 H 7.98 N 7.32

Further advantages and details of the invention result from the following claims.

Example 7

173 g of a solution of hydrogen chloride in DME (content 21.1% w/w=36.5 g (1.0 mole) HCl) were added dropwise to a suspension of 37.8 g (1.0 mole) sodium boron hydride and 51.3 g (0.25 mole) (S)-1-benzyl-3-hydroxy-2,5-pyrrolidinedione (IIa) in 300 ml DME within 2 h at 15°–20° C. The mixture was heated to 70° C. and, after addition of another 100 ml DME, agitated 3 h at 70° C. After cooling off, 80 ml MeOH were added dropwise and the batch was evaporated to dryness. The residue was taken up in 240 ml water and, after addition of 60 ml conc. hydrochloric acid, agitated at room temperature until the end of the development of gas. 300 ml toluene were added and the mixture was alkalized with 100 ml 30% sodium hydroxide solution. The toluene phase was separated off at 70° C., compounded with 100 ml water and 300 ml conc. hydrochloric acid and agitated overnight at room temperature. The mixture was then alkalized again with 50 ml 30% sodium hydroxide solution and the toluene phase separated off at 70° C. After filtration, the toluene phase was evaporated to dryness to yield 44.8 g (practically quantitative) (S)-1-benzyl-3-hydroxypyrrolidine (IIIa) as almost colourless oil. The structure of IIIa was corroborated by an NMR spectrum.

What is claimed is:

1. A method of producing optically active pyrrolidines with high enantiomeric purity of the general formula

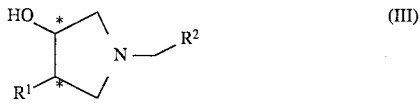 (III)

in which $R^1$ is hydrogen or a hydroxy group, $R^2$ is a phenyl group which can have one or more alkyl, alkoxy and/or halogen substituents, and * is an asymmetric center when the carbon atom so characterized carries a hydroxy group, comprising reducing enantiomerically pure 2,5-pyrrolidinediones of the general formula

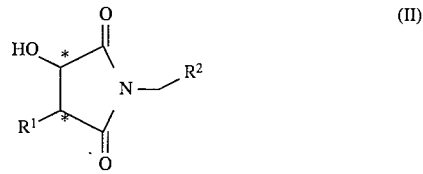 (II)

in which $R^1$, $R^2$ and * have the meanings indicated for formula (III), using an activated alkali borohydride.

2. The method according to claim 1, wherein the alkali borohydride is activated with iodine, sulfuric acid or hydrogen chloride.

3. The method according to claim 1 or 2, wherein the alkali borohydride is sodium or lithium boron hydride.

4. The method according to claim 1 or 2, further comprising carrying out the reaction in a solvent.

5. The method according to claim 4, wherein the reaction is carried out between −20° C. and the boiling temperature of the solvent used.

6. The method according to claim 4, wherein the solvent is an ether.

7. The method according to claim 5, further comprising the steps of hydrolyzing the reaction mixture after the end of the reduction by means of adding an alcohol, then water and an acid, alkalizing the reaction mixture, extracting the optically active pyrrolidines of general formula III with an organic solvent, and isolating the optically active pyrrolidines by evaporation of solvent, crystallization, or precipitation as hydrochloride.

8. The method according to claim 7, wherein the optically active 2,5 pyrrolidinediones of general formula II are produced by condensing optically active malic acid or tartaric acid with benzylamine in cumene, thereby producing an azeotropic mixture, and then azeotropically distilling off reaction water produced.

9. The method according to claim 8, wherein the optically active 2,5-pyrrolidinediones of general formula II are reduced without further purification.

* * * * *